United States Patent [19]
McDowell

[11] Patent Number: 6,143,035
[45] Date of Patent: Nov. 7, 2000

[54] IMPLANTED BONE STIMULATOR AND PROSTHESIS SYSTEM AND METHOD OF ENHANCING BONE GROWTH

[75] Inventor: Christopher Scott McDowell, Raynham, Mass.

[73] Assignee: Depuy Orthopaedics, Inc., Warsaw, Ind.

[21] Appl. No.: 09/239,497

[22] Filed: Jan. 28, 1999

[51] Int. Cl.$^7$ ..................................................... A61F 2/32
[52] U.S. Cl. .................................. 623/22.11; 623/18.11; 623/16.11; 607/50
[58] Field of Search .............................. 623/16, 18, 22, 623/16.11, 18.11, 22.11; 607/50, 51, 72, 75

[56] References Cited

U.S. PATENT DOCUMENTS

| | | | |
|---|---|---|---|
| 3,820,534 | 6/1974 | Kraus et al. | 623/16 X |
| 4,026,304 | 5/1977 | Levy | 623/16 X |
| 4,027,392 | 6/1977 | Sawyer et al. | 32/10 A |
| 4,175,565 | 11/1979 | Chiarenza et al. | 433/32 |
| 4,216,548 | 8/1980 | Kraus | 433/173 X |
| 4,665,920 | 5/1987 | Campbell | 607/51 |
| 4,798,206 | 1/1989 | Maddison et al. | 607/35 X |
| 5,030,236 | 7/1991 | Dean | 623/16 |
| 5,298,602 | 3/1994 | Shikinami et al. | 528/361 |
| 5,383,935 | 1/1995 | Shirkhanzadeh | 623/16 |
| 5,684,061 | 11/1997 | Ohnishi et al. | 523/114 |
| 5,759,205 | 6/1998 | Valentini | 433/173 X |

FOREIGN PATENT DOCUMENTS

| | | | |
|---|---|---|---|
| 1122329 | 11/1984 | U.S.S.R. | 607/51 |

OTHER PUBLICATIONS

Shokry, "Preliminary Study On The Use of A Silver Oxide Watch Battery (1.5 v) For Electrical Enhancement of Bone Healing", (1985) *Veterinary Research Communications*, 9: 245–250.

Hinsenkamp, "Electromagnetic Stimulation of Fracture Repair" (1978) *Acta Orthopedica Belgica*, Tome 44, Fasc. 5, pp. 671–698.

Hassler et al. "Studies on Enhanced Bone Healing Via Electrical Stimuli: Comparative Effectiveness of Various Stimulation Modalities" Nov. 6–10, 1976, 29$^{th}$ ACEMB *Sheraton–Boston, Boston, Massachusetts*, 16.1 p. 113.

Basset et al, "Generation of Electric Potentials by Bone in Response to Mechanical Stress", (1962) *Science* 137: 1063–1064.

*Primary Examiner*—Jeffrey A. Smith
*Attorney, Agent, or Firm*—Nutter, McClennen & Fish, LLP

[57] ABSTRACT

An implanted piezoelectric module generates charge which may be applied to tissue or used to power or recharge an implanted device such as a pump or pacemaker. In a system for enhanced bone healing or anchoring of an implanted bone prosthesis such as a plate, stem, articulation component or other structural component, the piezoelectric element is coupled to receive mechanical strain from body activity and generates a charge which is applied to enhance bone growth for anchoring the prosthesis. In one embodiment, the piezoelectric element is attached to a prosthetic hip stem on the medial side in a position on the shoulder or neck of the stem to preferentially undergo compressive strain. Preferably the element attaches near the surface and is poled such that its outer surface constitutes a negative electrode that operates to stimulate bone growth across an opposing receiving gap in the proximal femur. In another embodiment, an electrode lead extends distally from the piezoelectric element to apply the generated charge remotely thereto, such as at a prosthetic stem or fracture plate distal to the element itself. The piezo element may be located on a different bone. A metal mesh screen may apply the piezo-generated charge over a region of the bone surface to enhance growth of a thickening body at a desired region, for example at a region typically subject to stress shielding. The piezoelectric element may also be positioned in a region of tensile strain, with its cathodic pole extending to the desired growth gap or intended region of bone accretion. Oppositely poled elements may be positioned on opposing sides of a long bone or prosthesis so that the tensile and compressive stresses in opposed region produce charge of like polarity. Additional circuit elements may be attached to the implanted piezo elements to modulate or condition the charge electromechanically generated by the element and optimize its growth-stimulating effect.

17 Claims, 3 Drawing Sheets

IMPLANTED BONE STIMULATOR AND PROSTHESIS SYSTEM AND METHOD OF ENHANCING BONE GROWTH

BACKGROUND OF THE INVENTION

The present invention relates to bone prostheses and to methods for enhancing the anchoring of such prostheses or promoting the regrowth of bone in the vicinity of a prosthetic implant or other bone repair.

Replacement of a bone joint, or the splicing or repair of traumatic bone injury often involves the insertion or external attachment of an elongated member that spans a fracture, or that forms a joint termination for mechanical articulation with a mating part at the damaged portion of bone. Thus, for example, fractures may commonly be repaired with a bone plate which spans the break, or artificial joints such as knee or hip joints may utilize a prosthetic stem portion inserted into a long bone, that receives a corresponding prosthetic articulation portion attached to or articulated against the end of the stem portion for forming the replacement joint. In each case, the structural element of the prosthetic repair takes over a portion of the natural mechanical loading of the bone, but also requires regrowth of that bone in order for the prosthesis to become effectively attached to or incorporated in the bone.

It is known that healthy bone undergoes growth processes in which competing rates of bone resorption or wasting, and bone growth or accretion operate to maintain the requisite bone strength. Moreover, bone growth increases when the bone is subject to mechanical stress. Conversely, when a prosthetic stem or bone plate takes over the portion of the loading on a bone, and is anchored or transfers the load to a distal region, intermediate portions of bone may experience no natural loading, and tend to erode, an effect known as stress shielding. Much recent research in the area of prosthesis design has attempted to optimize the mechanical strength, e.g., the strain and bending deflection, of prosthetic elements, so as to match them to the characteristics of natural bone and assure that the requisite amount of loading continues to be transferred to surrounding bone to encourage the receiving residual bone to grow strong and bind to the prosthetic element.

At the physiological level, the mechanism whereby bone stresses result in enhanced bone growth or bone mass accretion are not fully elucidated. It has long been known that natural bone in mammals and even frogs has a piezoelectric property, and this has been attributed, for example, to the presence of hydroxy apatite in the bone itself. Experiments have shown that this active bone material is structured such that compression of the bone results in accumulation of a negative charge at the compressed surface, while tensile elongation produces charge of the opposite polarity. The property is intrinsic to the bone itself, and not to surrounding tissue or biological material, since the piezoelectric behavior has not been observed, for example, in tendon tissue or other non-boney structures, and it persists whether the bone is in vivo or ex vivo. Generation of charge has also been hypothesized to result from deformation of long chain molecules or other macro-molecules in the bone, based on the observation that removal of the organic fraction from natural bone may cause bone to either lose it piezoelectric property, or become so fragile as to render any charge undetectable.

In addition to the above observations on the electrogenic or charge-generating material present in natural bone, the presence of electrical potentials at the bone surface has been considered to promote bone healing, and several investigators have attempted, by applying currents or pulses of known shape, duration or energy, to experimentally assess the magnitude of this effect and to determine optimal regimens for enhancing post-operative healing. Conflicting results have been reported, with some investigators focusing on the desirability of a particular energy range and/or pulse duration during a limited post-operative time interval. As a matter of biophysics, it would seem apparent that a prolonged or excessively high DC potential would result in polarization shielding which is likely to interfere with natural processes governed by biologically available potentials applied to enzymatic or fluid transport mechanisms that may operate with the scale of tissue, cell and material mobility characteristic of a fracture site. In line with such expected effects, enhanced growth has been reported primarily for regimens involving relatively low frequency pulses at moderately low energies.

However, even when specific therapeutic effects appear to be demonstrated by the experimental data for a particular charge regimen, many practical problems are presented in terms of a delivery system for applying the desired charge pattern over a suitably long time interval. For example, one common approach suggests implanted or transdermal platinum electrodes, while another suggests an implanted power supply such a silver oxide battery or power source similar to that used for cardiac pacemakers, to enable the sustained application of an electric potential to the bone surface for an extended interval.

Accordingly it would be desirable to provide improved methods and devices for stimulating healing of fractures or implanted prostheses.

SUMMARY OF THE INVENTION

One or more of the foregoing desired ends are achieved in accordance with the present invention by a system for enhanced bone growth, for example, for anchoring an implanted bone prosthesis such as a plate, stem, articulation component or other structural component of fixed size to attach it to the bone. A piezoelectric element is electroded and oriented to produce a charge when subject to strain, and the element is implanted and fixed to either the bone, other tissue or to the prosthesis in a position subjected to a strain field so as to produce a polarized output. The negative electrode from the piezoelectric element attaches or extends to a bone gap or surface, providing a cathodic surface charge to enhance bone growth and solidify or promote anchoring of the prosthesis in the region of the electrode. In one embodiment, the piezoelectric element is attached on the medial side of a prosthetic hip stem in a position on the shoulder or neck of the stem, so that it preferentially undergoes compressive strain, and the element is poled to produce a negative charge when so strained. Preferably the element attaches near the surface such that its outer surface constitutes a negative electrode that operates to stimulate bone across an opposing receiving gap in the proximal femur. In another embodiment, the element attaches to tissue at a site different from the prosthesis, and an electrode lead extends distally from the piezoelectric element to apply the generated charge remotely, such as at a site proximate to a fracture plate. For such operation, the piezoelectric element may be installed in the natural bone, for example at the medial side of the femoral neck or other region of high or oriented strain, and its electrodes may extend to a site of fracture which may, for example, be further along the length of the femur or may be located on an adjacent bone. A conductive screw or metal mesh screen may attach to the bone fracture site to apply the piezo-generated charge over a region of the bone surface and enhance the buildup of a thickening body at the distal electrode site. Alternatively, the electrode may extend to another region of bone where growth is desired, for example, a region normally subject to stress shielding, such as the region of the proximal femur surrounding an implanted femoral stem component. In other embodiments, the piezoelectric element is positioned in a region of tensile strain, but it is oriented with its cathodic pole extending to the desired growth gap or intended region of bone accretion. Oppositely poled piezoelectric elements may be positioned on opposing sides of a long bone, so that all elements produce like charge. Alternatively, or in addition, circuit elements may be attached to the implanted piezo elements to condition the magnitude, duration or modulation of charge they produce. Furthermore, the piezoelectric element or elements may attach to the bone itself at a strain transfer position, and generate charge which is applied via one or more conductors to a bone gap around the prosthesis to enhance healing. The invention also contemplates conditioning and applying the piezo-generated charge to power an implanted device or to recharge a power cell for such a device.

BRIEF DESCRIPTION OF THE DRAWINGS

These and other features of the invention will be understood from the description below and claims herein, taken together with figures illustrating illustrative embodiments and operation of the invention, wherein:

DETAILED DESCRIPTION

Figures 1, 2:
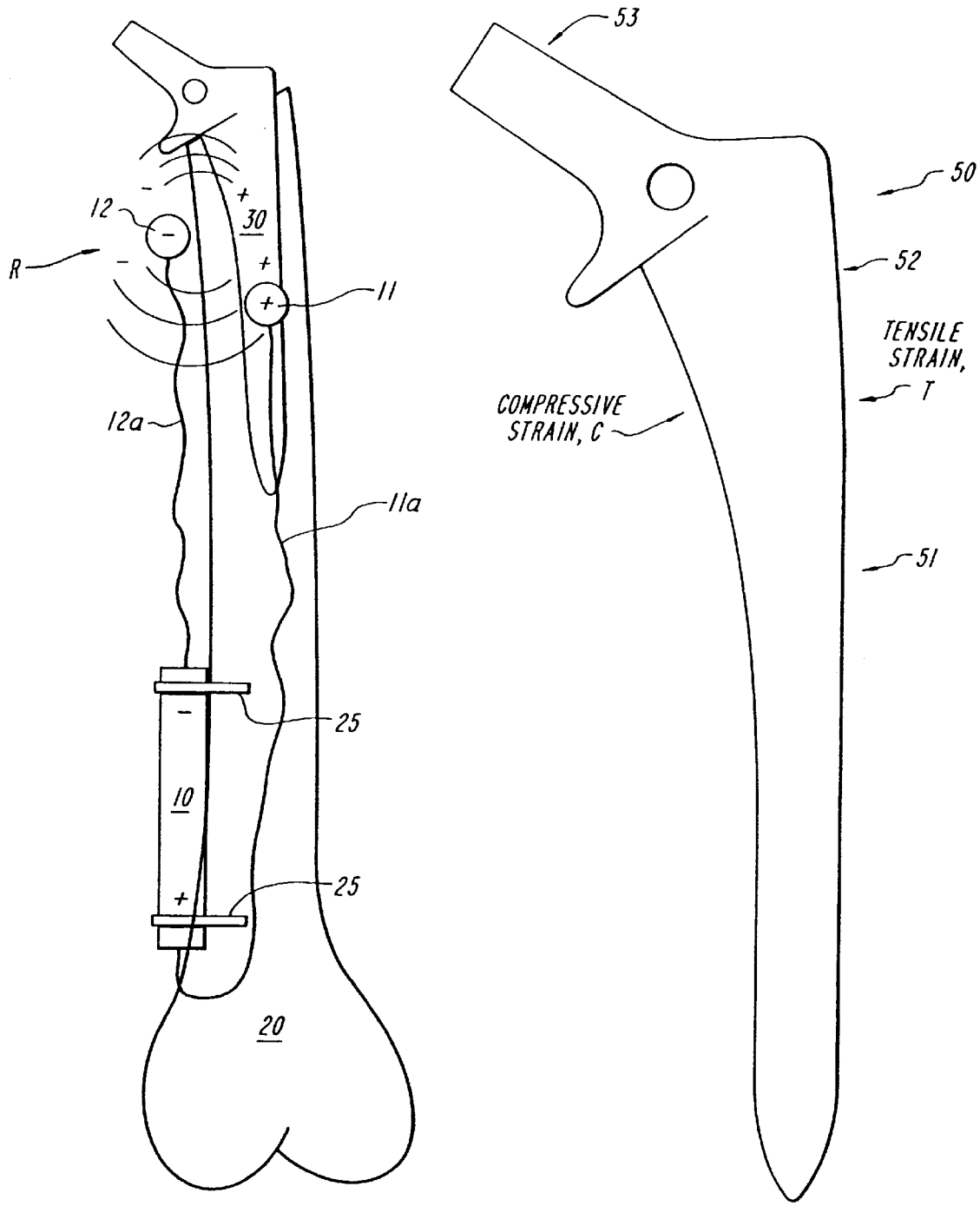
FIG. 1 shows a first embodiment of the invention.
FIG. 2 illustrates strain in a hip stem prosthesis.

As shown in FIG. 1, the present invention involves a system wherein, in its broadest terms, a piezoelectric element 10 is strain coupled to bone 20 or other body tissue so as to generate charge as the tissue undergoes strain, and the generated charge is applied via electrodes 11, 12 to a region R where it is desired to stimulate bone growth. For purposes of illustration, such a system is shown in FIG. 1 as utilizing a separate piezoelectric element attached by pins or bone screws 25 to a lower end of an intact bone, such as the femur, and the poles of the piezoelectric element are connected via leads 11a, 12a to carry the charge remotely and couple the charge to promote healing. As illustrated, the positive or anode side is coupled to a prosthetic implant 30, shown as a hip stem, and the negative or cathode side is coupled to a region of bone along the medial edge of the proximal femur to enhance bone growth in that region. In this manner, the bone is made negative with respect to the prosthetic stem to enhance filling of the canal and closing of gaps between the stem and bone.

Thus, strains from the natural loading of the tissue (e.g., bone 20) are coupled into the piezoelectric element and generate a voltage across the poles of that element which is brought out via the electrode leads and applied to create a current flow between the prosthetic stem and surrounding bone tissue, in which the bone is cathodic.

In general, the direction of current flow induced in vivo will be dependent on the pole orientation of the piezoelectric element and the direction of strain loading e.g., tensile or compressive strain, applied to the element. In further aspects of the invention these are selected or controlled during piezo manufacture so that implantation of the bulk electroded piezo material produces enhanced bone growth effects. Advantageously, the frequency of the current flow generated by strained tissue in this manner is comparable to the frequency of current flow which occurs in natural bone as a result of natural piezoelectric effects during normal activity. Moreover, the piezoelectric element 10 is preferably completely sealed and is implanted as a permanent device, so that it operates to sustain or maintain bone growth during the life of the implant.

The configuration illustrated in FIG. 1 is schematic and may be varied to suit different prostheses, tissue configurations or bone growth requirements. For example, when the prosthesis is simply a plate attached to join ends or pieces of a fractured bone, the output of the piezoelectric element may be connected to stimulate growth at the plate so as to accelerate the joining of the fractured parts. In that case, the piezoelectric element itself may be connected to the same or to a different bone, and it may even be connected across the fracture site so that it experiences the level of strain that is applied across that region. Since strain will increase when the site is flexed more (i.e. is weaker), the output adapts to the degree of stimulation needed.

In general, the charge produced by the piezoelectric element may be conditioned by circuit elements, or its amplitude and polarity may be controlled at an earlier stage of fabrication by the selection of piezo material, so that it has suitable voltage and current characteristics for bone stimulation. By way of example, a peak current of about 250 $\mu$A and a voltage level of about several mV per centimeter of bone in the current path would be within the appropriate target range to produce a signal for promoting bone growth. Signal conditioning may be effected by providing small circuit elements across the piezo output, such as diode to pass output of one polarity (when it is coupled to tissue that is strained bidirectionally) or to limit voltage, or such as shunt resistors or capacitors to shape or condition the output signal.

In one preferred embodiment, the piezo element forms a compact assembly which is intimately affixed to the body of the prosthetic implant 30 prior to surgery e.g., during manufacture. For example, in such an embodiment, the piezo element may take the form of a plate which is fitted into a dovetail slot of the prosthesis and is bonded thereto, so as to effectively couple the strain from an elongated area of the surface of the prosthesis and be energized thereby. Several relevant considerations for such fabrication will now be discussed in relation to a hip stem prosthesis as shown in FIG. 1.

FIG. 2 illustrates a prosthetic hip stem 50 for which measurement or mechanical modeling has identified regions of high strain in the device. As shown, the stem 50 has a generally elongated form with a lower body portion 51 fabricated in a generally spike-like shape for insertion into a prepared femoral canal, and a widening shoulder region 52 which fits within the spout of the proximal femur and supports a trunnion or post 53 to which a prosthetic hip ball attaches as part of a total joint replacement. The weight-bearing path from the hip to trunion along the medial side of the prosthesis downward, results in a region of compressive strain, denoted C, on the medial side of the shoulder region, and a region of tensile or extensional strain, denoted T, on the lateral side of the prosthesis. During a normal surgical procedure, a stem such as stem 50 is driven into a prepared femur 20 and seated against the bone. However, the shape of the prepared bone cannot exactly match the prosthesis, and numerous gaps remain particularly in the upper tapered region of the proximal canal where a bone gap may remain at one or more regions around the prosthesis. Following implantation, these gaps may fill as bone grows during normal healing. However, as noted above, numerous competing factors govern the rate of bone growth; when the prosthesis itself shields a region from receiving stress, bone may fail to re-grow in that region. This problem may be further compounded when looseness in the original fitting produces wear processes that erode bone more quickly than it can grow, or creates debris which promotes an osteolytic response.

Figure 2A:
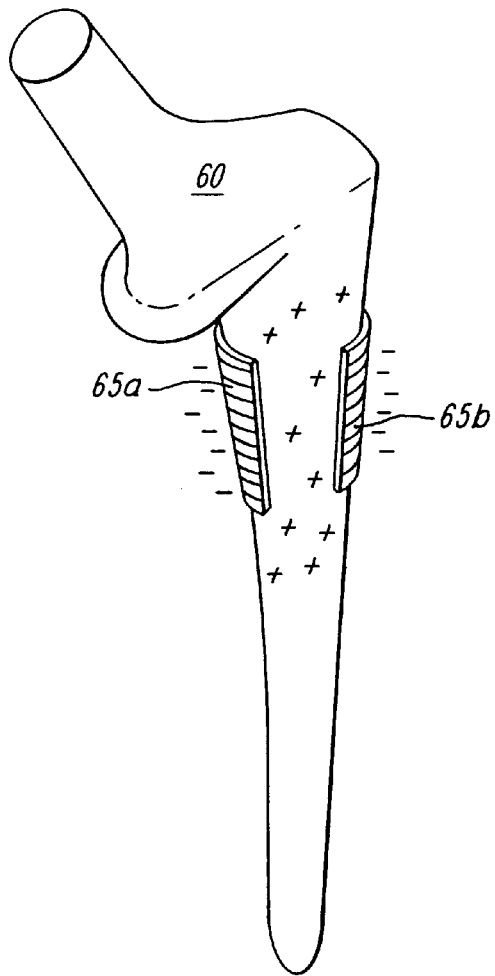
FIG. 2A illustrates a second embodiment of the invention.

As shown in FIG. 2A, bone healing is enhanced in accordance with this embodiment of the invention by providing a prosthetic implant 60 having one or more piezoelectric elements 65a, 65b fitted to the prosthesis to apply cathodic or bone-stimulating electric fields around the prosthesis itself. As shown in FIG. 2A, a first piezoelectric element 65a is attached in the region C of compressive strain, and an oppositely poled piezoelectric element 65b is attached in the region T of tensile strain. By arranging oppositely poled elements in regions of oppositely directed strain, each has its prosthesis-contacting electrode produce an output of the same polarity in normal active stimulation. As illustrated, the elements are placed with the negative pole oriented toward the surrounding bone tissue, and their opposite (positive) side contacting the implant to render the prosthesis anodic.

This results in an electrical field around the implant wherein tissue is electronegative with respect to the implanted stem, causing bone to grow into and refill the femoral canal. In alternative embodiments, bone growth can be promoted on the surface of the implant itself by connecting the piezo elements to make the implant cathodic.

In either case, the conductive metal prosthesis distributes electrical charge over a larger region than the pole of a localized piezo element. In general, the stimulated region may also be selected or tailored by employing electrodes having a larger or smaller surface area, for example, by connecting a special conductive screen, or a plurality of separate electrode leads, to preferentially enhance the applied field at one or more local or defined regions. The degree of natural tissue conductivity is believed to be sufficient so that the appropriate field may be established over a region by providing a single or only a few discrete wire or contact electrodes to the bone itself.

While two charge generating elements are illustrated in FIG. 2A, the device may have fewer or more piezoelectric elements, and by employing leads, the electrodes may be positioned at remote sites. Alternatively, the system may employ some elements with exposed electrode surfaces of the piezo elements or packaged piezoelectric elements, and some with insulated distal leads to suit the available sites of tissue strain and the possible different loci where bone growth is intended.

In general it is desirable to have the piezo elements entirely encapsulated or otherwise rendered suitable for long-term implantation. Because only a relatively small electrical signal is required, certain naturally occurring hardy piezoelectric materials such as quartz crystal slices may suitably be employed as generators when mechanically coupled to the prosthesis. Alternatively, high tech piezoceramic or piezopolymer elements may be formed in suitable configurations. Thus, for example, suitably shaped sheets, blocks or plates of hard piezo material such as the piezoceramic PZT may be arranged in a cutout, dovetail or slot in the prosthesis itself. Furthermore, these elements may be poled during assembly of the prosthesis to achieve the desired polarity or charge orientation. When the charge is to be generated remotely from the prosthesis or patch, it may be generated by such stiff piezoelements coupled to bone, or by pads or membranes containing less stiff materials, such as PVDF polymer, coupled to softer tissue or mounted between rigid attachments. Other variations will occur to those skilled in the art to adapt the piezo charge generators to commonly used prostheses and to the available biological sites of attachment or regions suitable for applying tissue strain energy.

Figure 3:
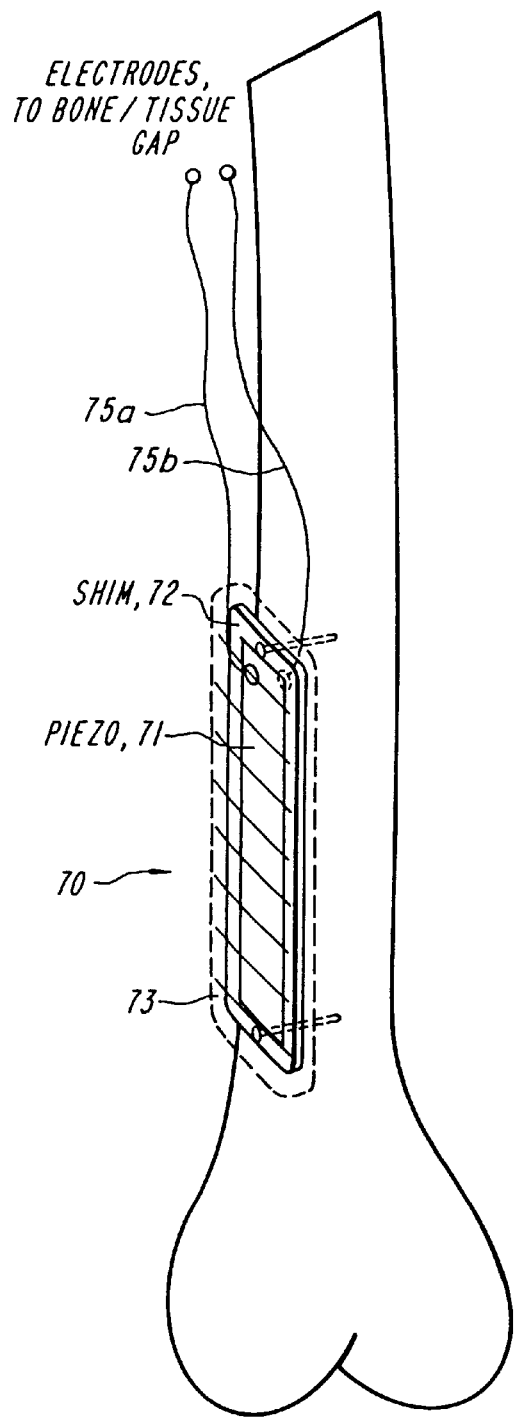
FIG. 3 illustrates a third embodiment of the invention.

FIG. 3 illustrates another embodiment of the invention. In this construction a piezoceramic element 71 is mounted within an assembly 70 that further includes a flexible metal or plastic shim 72, and a polymeric cover or casing 73 to enclose both the shim and piezo. The piezo element is stiffly attached to the shim, so that any strain or flexing of the shim gives rise to a charge in the piezo, and the ends of the shim are each pinned to the bone 20, preferably near its middle or thinnest region where the pinned end regions will cause the shim 72 to undergo the greatest strain or displacement. Electrode leads 75a, 75b extend from the package to apply the flex-generated charge remotely, for example, to a prosthetic stem, a bone plate or bone screw. Bone screws may be thus negatively charged to energize the bone in which they are inserted, while plates may serve as anodic counterelectrodes to position the bone at a relatively negative potential, or may serve as cathodes to bias the bone to which they are attached. This construction allows charge generators to be conveniently installed in secure locations, independently of the prosthesis installation site. While FIG. 3 illustrates a stiff flexible piezo attached to a shim structure in which the tissue strain induces bending, the invention further contemplates packages formed of or containing piezopolymer material which may be sutured to soft tissue, or flexible packages such as rubber blocks or pads, in which loading forces are transferred to piezo strain transducers embedded in the rubber body when suitably positioned or attached next to moving tissue or strained tissue.

Figure 4:
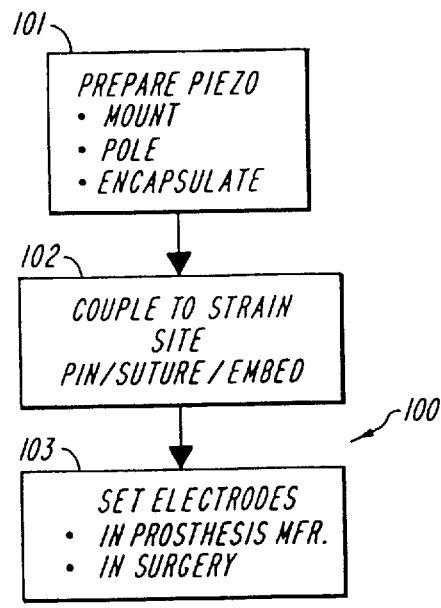
FIG. 4 illustrates steps of the method of the present invention.

FIG. 4 illustrates the basic steps of a method 100 of the present invention. As shown therein, as a first step 101 a piezoelectric element is prepared to suitably generate charge when implanted. Preparation may take any of several forms including the encapsulation of the element, the forming of the element into a plate or block-like member which may be attached to a prosthesis, embedding of the element in an elastic or a stiff member which may sutured to tissue or pinned to bone to experience strain during the activities of daily living, and other ancillary steps such as the forming of electrodes, attachment of remote leads in a biologically compatible manner or otherwise preparing a piezoelectric element for implantation in the intended environment to generate charge.

As a second step 102, the piezo element is strain-coupled to either the prosthesis itself, or to a body tissue site where it will experience the strain necessary to generate charge. In the case of attachment to a prosthesis, this step may be included as part of the prosthesis manufacturing step, for example, by embedding a piezoelectric plate in a slot milled in a femoral stem, or embedding piezoelectric material in a region of a bone plate where it may act as a load cell or strain sensor to generate the required charge. For the embodiments in which the piezoelectric element is separate from the prosthetic element, this step may involve suturing or pinning the charge generating element or its support to the respective soft or hard body tissue.

Finally, the third step 103 is to set the electrodes to promote bone growth. As for the first two steps above, this step may subsumed under the manufacturing of the prosthesis itself when the electrodes and piezo element are both integrated into the prosthesis body. Thus, for example, as shown in FIG. 2A, the elements may be attached to a metal prosthesis in such a manner that one charged electrode surface of the element is exposed to position a negative-going gradient at the facing bone and promote bone growth. The other piezo electrode energizes the surface of the prosthesis to serve as the anode for current flow through surrounding bone. Alternatively, as described in regard to FIG. 1, the electrode attachments may be brought out via leads, and auxiliary plates or electrode screens if necessary, to place the desired charge in a specific region remote from the element itself where bone growth is to be enhanced.

In each case the invention contemplates that normal activities of daily living will provide the strain that powers and continues to generate charge during life of the implant so that even when portions of bone remain unattached or disconnected, and thus cannot experience sufficient strain to generate their own growth enhancing charges, the electrodes of the element will promote bone growth in the desired or targeted regions.

While normal biological activity may be expected to produce suitable slowly varying strains, for example, having a frequency on the order of 1 Hz, so that changing charge generates a voltage signal to create a bone-stimulating electric field, the invention also contemplates that charge conditioning or signal shaping elements may also be included in the packaged piezoelectric element or conductors therefrom so as to generate specific signals appropriate for bone stimulation. Thus, for example, a charge storage element and oscillator, or a resonant or periodic shunt may operate to convert the piezo output to a pulsed electric field, or create other wave form or duty cycle different from that of the natural strain field of the underlying tissue.

The invention further contemplates the provision of implanted piezo element as described above which is configured to apply the charge it generates to an electrical device. In accordance with this aspect of the invention, a charge generating element, as illustrated for example in FIGS. 1, 2A or 3 above, provides its output to charge conditioning and charge storage elements so as to produce an electrical signal having useful amplitude and power. By way of example, the output may be applied by way of a voltage-limiting shunt to a rectifying diode or bridge to charge a capacitor, or to charge a rechargeable battery or power cell which serves as a storage element. The storage element, in turn, provides a sustained voltage and current for device operation. Configured in this manner, the piezo module may be used as the primary power source for an implanted device such as an intermittently-operated infusion pump, or may serve as a recharger or secondary power source for a battery powered device such as a cardiac pacemaker.

Figure 4A:
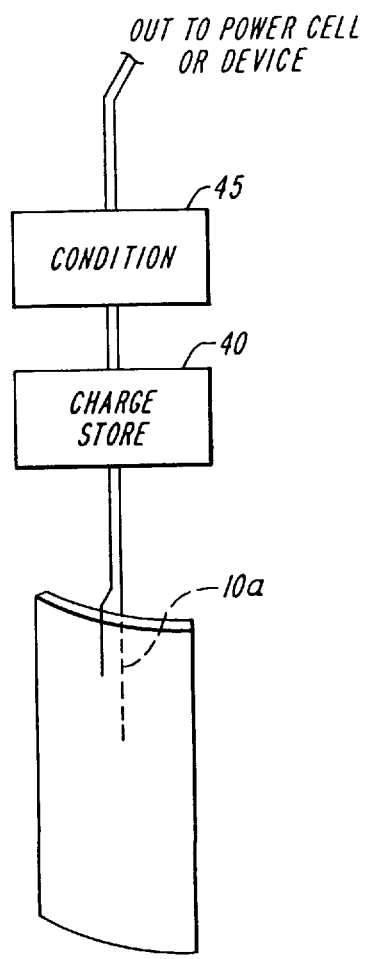
FIG. 4A is a schematic illustration of a fourth embodiment of the invention.

FIG. 4A illustrates such a device. An implanted piezo module 10*a* which attaches to tissue or is incorporated in a prosthesis is connected in a load-bearing or strain transfer position to generate charge, and the output is applied to a charge storage unit 40, such as a capacitor, and to a conditioning circuit 45. The nature of the storage and conditioning will vary depending on the intended device application. Thus, for example, if the conditioned output is to be applied to an infusion pump that operates intermittently and only draws a brief current burst, simply charging a capacitor may be sufficient to provide the desired current flow for a sufficient time. If the output is to power a processor or the like, the conditioning circuit may be configured to convert the piezo charge to continuous power at a defined voltage level, or to provide charging signals for a power cell that provides the desired continuous output.

In such case, the original signal arising at the frequency of natural bone or muscle loading, is changed in amplitude, duration or power to suit the requirements of the intended output device. Advantageously, however, the output may be greatly increased in voltage or current, and may be shaped or transformed—for example into modulated pulses for charging a battery—so as to provide a perpetual internal power source for an implanted medical device. Moreover, by incorporating the piezo module in a prosthesis as shown in FIG. 2A, an exceptionally hardy, enclosed generator with well-controlled power specifications is achieved.

The invention being thus described and illustrative embodiments illustrated herein, further variations and modifications will occur to those skilled in the art, and all such variations and modifications are considered to be within the scope of the invention as defined by the claim appended hereto and equivalents thereof.

What is claimed is:

1. A system for enhanced anchoring of an implanted bone prosthesis of the type wherein the prosthesis comprises a plate, stem, articulation component or other structural component for attaching to the bone at a first location, wherein the system comprises a generator body including a strain response element formed of piezoelectric material and being configured for implantation at a second location to receive strain and generate charge in response thereto, and at least one output electrode connected to said generator body, said output electrode extendingto said first location for applying the charge generated by the generator body to said first location as a signal of defined polarity to enhance bone growth in the vicinity of the prosthesis.

2. The system of claim 1, wherein said output electrode is configured to apply said charge at a prosthesis surface adjacent a fitting bone gap.

3. The system of claim 1, further comprising means for attaching the strain responsive element to the prosthesis.

4. The system of claim 3, wherein the output electrode includes an electrode surface in the immediate vicinity of said strain responsive element.

5. The system of claim 3, wherein said output electrode extends remotely from said strain responsive element to apply said signal of defined polarity to a region of bone subject to stress shielding by the prosthesis.

6. The system of claim 1, wherein said strain responsive element is sealed in a flexible body implantable proximate to the prosthesis for applying electricity in the vicinity thereof.

7. The system of claim 1, wherein said strain responsive element is configured to fit against a surface of a prosthesis to develop an electrical signal from strain in the prosthesis.

8. The system of claim 7, wherein said strain responsive element is configured to power an electrical device coupled to said prosthesis.

9. The system of claim 1, further comprising a prosthesis, and wherein said strain responsive element is mounted in a region of high strain of said prosthesis, and applies said generated electrical energy to a bone gap about said prosthesis.

10. The system of claim 9, wherein the prosthesis is a femoral stem and said strain responsive element is positioned on the medial side of the stem to operate under compressive strain.

11. The system of claim 9, wherein the prosthesis is a femoral stem and said strain responsive element is poled and positioned in a region of strain such that a first electrode of the element is predominantly cathodic, and said output electrode couples energy of the first electrode to a region of desired bone stimulation.

12. The system of claim 1, wherein the generator body is adapted to couple to a bone for generating charge responsive to strain in the bone.

13. The system of claim 1, wherein the generator body is a flexible body adapted to couple to soft tissue.

14. An electrical charge generation system for medical use, such system comprising a piezoelectric transducer configured for implantation and strain coupling to tissue within a human body so that the transducer generates charge in response to normal musculoskeletal movement of the body and said transducer applies said generated charge to output electrodes, and means for conditioning charge of said output electrodes for application to an implanted device, wherein said means for conditioning charge conditions the charge to form a signal effective for stimulating bone growth adjacent to the implanted device.

15. The system of claim 14, wherein said means for conditioning charge forms a signal effective for powering the implanted device.

16. The system of claim 15, wherein said means for conditioning charge forms a signal effective for recharging a power cell.

17. A method of enhancing bone growth, such method comprising the steps of
   a) configuring a piezoelectric material for
      i) implantation in a living body, and
      ii) receiving strain form tissue when the body is active such that the material generates charge in response to received strain; and
   b) providing electrodes connected to said material and configured for applying the generated charge remotely to a region along a bone so as to form an electric field between the bone and a bone prosthesis and stimulate growth of bone in said region, and
   c) implanting the piezoelectric material such that said electrodes apply said charge to said region whereby strain from body activity stimulates said bone growth.

* * * * *